US00PP28825P3

(12) United States Plant Patent
van den Haak

(10) Patent No.: US PP28,825 P3
(45) Date of Patent: Dec. 26, 2017

(54) ***ECHINACEA* PLANT NAMED 'APECSSIRED'**

(50) Latin Name: *Echinacea hybrida*
Varietal Denomination: Apecssired

(71) Applicant: Jelle van den Haak, Amsterdam (NL)

(72) Inventor: Jelle van den Haak, Amsterdam (NL)

(73) Assignee: Gootjes-Allplant B.V., Schagen (NL)

( * ) Notice: Subject to any disclaimer, the term of this patent is extended or adjusted under 35 U.S.C. 154(b) by 53 days.

(21) Appl. No.: 14/999,191

(22) Filed: Apr. 8, 2016

(65) Prior Publication Data

US 2017/0295706 P1 Oct. 12, 2017

(51) Int. Cl.
*A01H 5/02* (2006.01)

(52) U.S. Cl.
USPC ..... Plt./428

(58) Field of Classification Search
USPC ..... Plt./263.1, 428
See application file for complete search history.

*Primary Examiner* — Susan McCormick Ewoldt
*Assistant Examiner* — Karen Redden
(74) *Attorney, Agent, or Firm* — C. A. Whealy

(57) ABSTRACT

A new and distinct cultivar of *Echinacea* plant named 'Apecssired', characterized by its broadly upright and relatively compact plant habit; moderately vigorous growth habit; freely branching habit; strong flowering stems; numerous large single-type inflorescences with red-colored ray florets and orangish red-colored receptacle spines; and good garden performance.

3 Drawing Sheets

Botanical designation: *Echinacea hybrida.*
Cultivar denomination: 'APECSSIRED'.

BACKGROUND OF THE INVENTION

The present invention relates to a new and distinct cultivar of *Echinacea* plant, botanically known as *Echinacea hybrida*, and hereinafter referred to by the name 'Apecssired'.

The new *Echinacea* plant is a product of a planned breeding program conducted by the Inventor in Hazerswoude-Dorp and Andijk, The Netherlands. The objective of the breeding program is to develop new vigorous *Echinacea* plants with unique and attractive ray floret coloration.

The new *Echinacea* plant originated from an open-pollination in July, 2013 in Hazerswoude-Dorp, The Netherlands of an unnamed proprietary selection of *Echinacea hybrida*, not patented, as the female, or seed, parent with an unknown selection of *Echinacea hybrida* as the male, or pollen, parent. The new *Echinacea* plant was discovered and selected by the Inventor as a single flowering plant from within the progeny of the stated open-pollination grown in a controlled greenhouse environment in Hazerswoude-Dorp, The Netherlands in August, 2014.

Asexual reproduction of the new *Echinacea* plant by tissue culture in a controlled environment in Andijk, The Netherlands since 2015 has shown that the unique features of this new *Echinacea* plant are stable and reproduced true to type in successive generations.

SUMMARY OF THE INVENTION

Plants of the new *Echinacea* have been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Apecssired'. These characteristics in combination distinguish 'Apecssired' as a new and distinct *Echinacea* plant:

1. Broadly upright and relatively compact plant habit.
2. Moderately vigorous growth habit.
3. Freely branching habit.
4. Strong flowering stems.
5. Numerous large single-type inflorescences with red-colored ray florets and orangish red-colored receptacle spines.
6. Good garden performance.

Plants of the new *Echinacea* can be compared to plants of the female parent selection. Plants of the new *Echinacea* differ primarily from plants of the female parent selection in growth habit as plants of the new *Echinacea* are more uniform than plants of the female parent selection.

Plants of the new *Echinacea* can be compared to plants of *Echinacea hybrida* 'Hot Summer', disclosed in U.S. Plant Pat. No. 20,687. In side-by-side comparisons, plants of the new *Echinacea* differ primarily from plants of 'Hot Summer' in the following characteristics:

1. Plants of the new *Echinacea* are more compact than plants of 'Hot Summer'.
2. Plants of the new *Echinacea* are more vigorous than plants of 'Hot Summer'.
3. Plants of the new *Echinacea* are more freely branching than plants of 'Hot Summer'.
4. Plants of the new *Echinacea* and 'Hot Summer' differ in ray floret color as plants of 'Hot Summer' have deep red-colored ray florets.

BRIEF DESCRIPTION OF THE PHOTOGRAPHS

The accompanying photographs illustrate the overall appearance of the new *Echinacea* plant showing the colors as true as it is reasonably possible to obtain in colored reproductions of this type. Colors in the photographs may differ slightly from the color values cited in the detailed botanical description which accurately describe the colors of the new *Echinacea* plant.

The photograph on the first sheet is a side perspective view of a typical flowering plant of 'Apecssired' grown in a container.

The photograph on the second sheet is a close-up view of a typical flowering plant of 'Apecssired' featuring the leaves.

The photograph on the third sheet is a close-up view of a typical flowering plant of 'Apecssired' featuring the inflorescences.

DETAILED BOTANICAL DESCRIPTION

The aforementioned photographs and following observations and measurements describe plants grown during the summer in 17-cm containers in an outdoor nursery in Mijdrecht, The Netherlands and under cultural practices typically used in commercial *Echinacea* production. During the production of the plants, day temperatures ranged from 10° C. to 25° C. and night temperatures ranged from 4° C. to 15° C. Plants were pinched eight weeks after planting and were six months old when the photographs and description were taken. In the following description, color references are made to The Royal Horticultural Society Colour Chart, 2015 Edition, except where general terms of ordinary dictionary significance are used.

Botanical classification: *Echinacea hybrida* 'Apecssired'.

Parentage:

- *Female parent*.—Unnamed proprietary selection of *Echinacea hybrida*, not patented.
- *Male parent*.—Unknown selection of *Echinacea hybrida*, not patented.

Propagation:

- *Type*.—By tissue culture.
- *Time to initiate roots, summer*.—About twelve days at temperatures about 20° C.
- *Time to initiate roots, winter*.—About 16 days at temperatures about 20° C.
- *Time to produce a rooted young plant, summer*.—About 36 days at temperatures about 18° C.
- *Time to produce a rooted young plant, winter*.—About 42 days at temperatures about 18° C.
- *Root description*.—Thick, fleshy; typically white in color, actual color of the roots is dependent on substrate composition, water quality, fertilizer type and formulation, substrate temperature and physiological age of roots.
- *Rooting habit*.—Moderately freely branching; sparse.

Plant description:

- *Plant form and growth habit*.—Herbaceous perennial; broadly upright and relatively compact plant habit, relatively broad inverted triangle; freely basal branching habit with about 13 lateral branches developing per plant; moderately vigorous growth habit.
- *Plant height*.—About 46.8 cm.
- *Plant diameter or spread*.—About 54 cm.
- *Lateral branches*.—Length: About 33.3 cm. Diameter: About 5 mm. Internode length: About 4.8 cm. Aspect: Erect to about 40° from vertical. Strength: Strong. Texture: Densely pubescent; strigose, rough. Color: Close to 146B; stems exposed to direct sunlight are tinged with close to N199A.

Leaf description:

- *Arrangement*.—Alternate, simple.
- *Length*.—About 14.1 cm.
- *Width*.—About 5.9 cm.
- *Shape*.—Ovate to narrowly ovate.
- *Apex*.—Acute to narrowly acute.
- *Base*.—Attenuate.
- *Margin*.—Entire to shallowly dentate.
- *Texture and luster, upper surface*.—Moderately to densely pubescent, strigose and rough; matte.
- *Texture and luster, lower surface*.—Moderately to densely pubescent, strigose and rough; slightly glossy.
- *Venation pattern*.—Pinnate.
- *Color*.—Developing leaves, upper surface: Close to 143B. Developing leaves, lower surface: Close to 144B. Fully expanded leaves, upper surface: Close to NN137B; venation, close to 144A. Fully expanded leaves, lower surface: Close to 137B; venation, close to 144B.
- *Petioles, basal leaves*.—Length: About 11.3 cm. Diameter: About 2.5 mm by 3.5 mm. Texture and luster, upper surface: Glabrous; moderately glossy. Texture and luster, lower surface: Glabrous; glossy. Color, upper surface: Center, close to 144A; towards the margins, close to NN137B. Color, lower surface: Center, close to 144A; towards the margins, close to 137A.

Inflorescence description:

- *Appearance*.—Large single-type inflorescences with ray and disc florets arranged on a capitulum; inflorescences positioned upright above the foliar plane on mostly upright and strong peduncles.
- *Flowering habit*.—Freely flowering habit with about 40 inflorescences per plant.
- *Fragrance*.—Faintly; sweet and pleasant.
- *Time to flower*.—Plants flower continuously from mid-July to late November in The Netherlands.
- *Inflorescence longevity*.—Inflorescences maintain good substance for about three weeks on the plant; inflorescences persistent.
- *Inflorescence buds*.—Height: About 2.2 cm. Diameter: About 2.3 cm. Shape: Flattened globular. Color: Darker than 146A; ray florets, close to 180D.
- *Inflorescence size*.—Diameter: About 10.2 cm. Depth (height): About 4.1 cm. Disc diameter: About 3.3 cm.
- *Receptacles*.—Height: About 6 mm. Diameter: About 8 mm. Color: Close to 155B.
- *Ray florets*.—Quantity and arrangement: About 22 arranged in a single whorl at the base of the receptacle. Length: About 4.4 cm. Width: About 1.05 cm. Shape: Oblanceolate to narrowly obovate. Apex: Emarginate to praemorse. Base: Cuneate. Margin: Entire. Texture and luster, upper surface: Glabrous; velvety and matte. Texture and luster, lower surface: Glabrous; moderately glossy. Aspect: Horizontal to slightly downward, about 10° from horizontal. Color: When opening, upper surface: Close to 53B to 53C. When opening, lower surface: Close to 54A to 54B. Fully opened, upper surface: Close to 53B; towards the apex, tinged with close to 42B; with development, color becoming closer to 29B. Fully opened, lower surface: Close to 59D; with development, color becoming closer to 38B.

*Disc florets*.—Quantity and arrangement: About 240 per inflorescence, arranged spirally at the center of the inflorescence. Length: About 1.1 cm. Diameter: About 2.5 mm. Shape: Tubular; proximally, 20% free, not fused. Apex: Acute. Base: Fused. Margin: Entire. Texture and luster, inner and outer surfaces: Smooth, glabrous; glossy. Color, when opening, inner and outer surfaces: Apex: Close to 178A. Mid-section: Close to 199B. Base: Close to N144B. Color, fully opened, inner and outer surfaces: Apex: Close to 178B. Mid-section and base: Close to 150C.

*Receptacle spines*.—Quantity: One per disc floret. Shape: Acicular. Apex: Acute. Base: Attenuate. Texture and luster: Smooth, glabrous; glossy. Color: Apex: Close to 44B. Mid-section and base: Close to 144A.

*Involucral bracts*.—Quantity per inflorescence: About 60 arranged in about four whorls. Length: About 7 mm. Width: About 3 mm. Shape: Ovate to narrowly ovate. Apex: Acute. Base: Cuneate. Margin: Entire. Texture and luster, upper surface: Smooth, glabrous; matte. Texture and luster, lower surface: Densely pubescent; matte. Color, upper surface: Close to NN137A. Color, lower surface: Close to 178A; towards the margins and base, close to 137C.

*Peduncles*.—Length: About 5.8 cm. Diameter: About 4.5 mm. Strength: Strong. Aspect: Upright to about 20° from vertical. Texture: Moderately pubescent; strigose. Color: Close to 146B; peduncles exposed to direct sunlight are tinged with close to N199A and N200A.

*Reproductive organs*.—Androecium (present on ray and disc florets): Quantity per floret: Five. Filament length: About 3.5 mm. Filament color: Close to 157C to 157D. Anther length: About 3 mm. Anther shape: Lanceolate. Anther color: Close to 197A and 202A. Pollen amount: Moderate. Pollen color: Close to 17B. Gynoecium (present only on disc florets): Quantity per floret: One. Pistil length: About 7 mm. Stigma shape: Decurrent, unequal. Stigma color: Close to N186C. Style length: About 6 mm. Style color: Close to 145B to 145C. Ovary color: Close to 150D. Seeds and fruits: Seed and fruit development have not been observed on plants of the new *Echinacea*.

Disease & pest resistance: Plants of the new *Echinacea* have not been shown to be resistant to pathogens and pests common to *Echinacea* plants.

Garden performance: Plants of the new *Echinacea* have exhibited good garden performance and to tolerate rain and wind. Plants of the new *Echinacea* have been observed to tolerate high temperatures of about 35° C. and to be hardy to USDA Hardiness Zones 3 to 4.

It is claimed:

1. A new and distinct *Echinacea* plant named 'Apecssired' as illustrated and described.

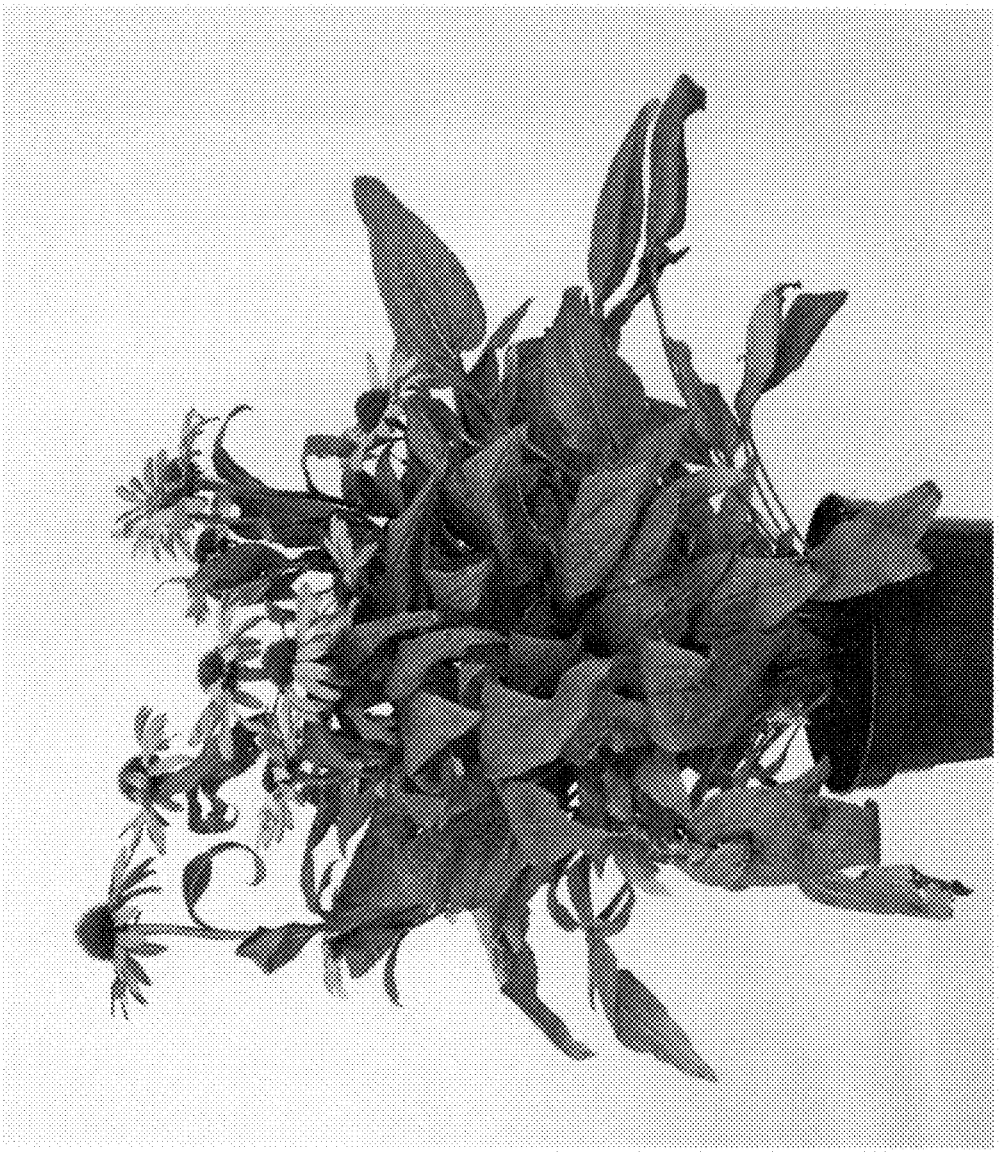

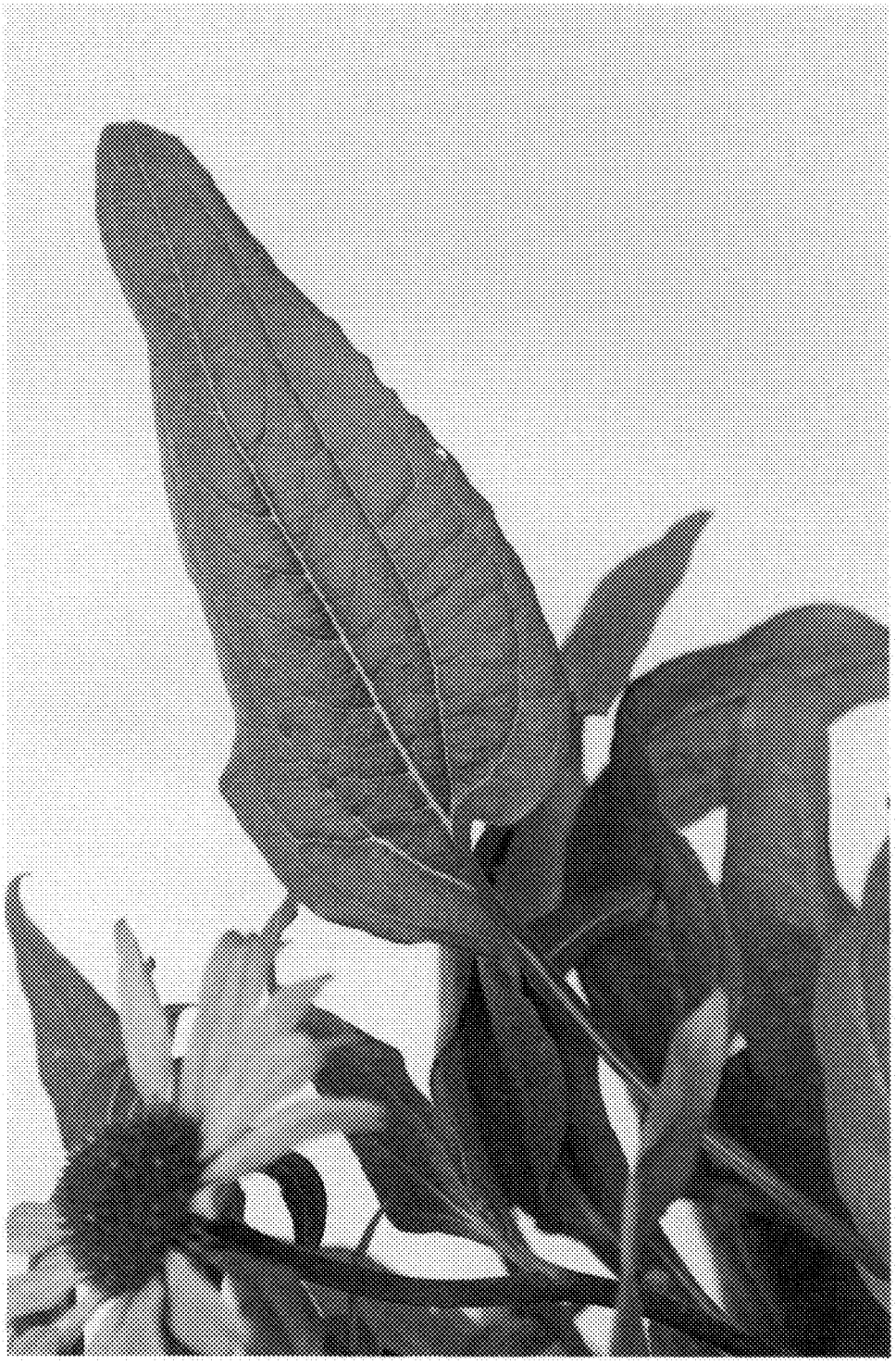

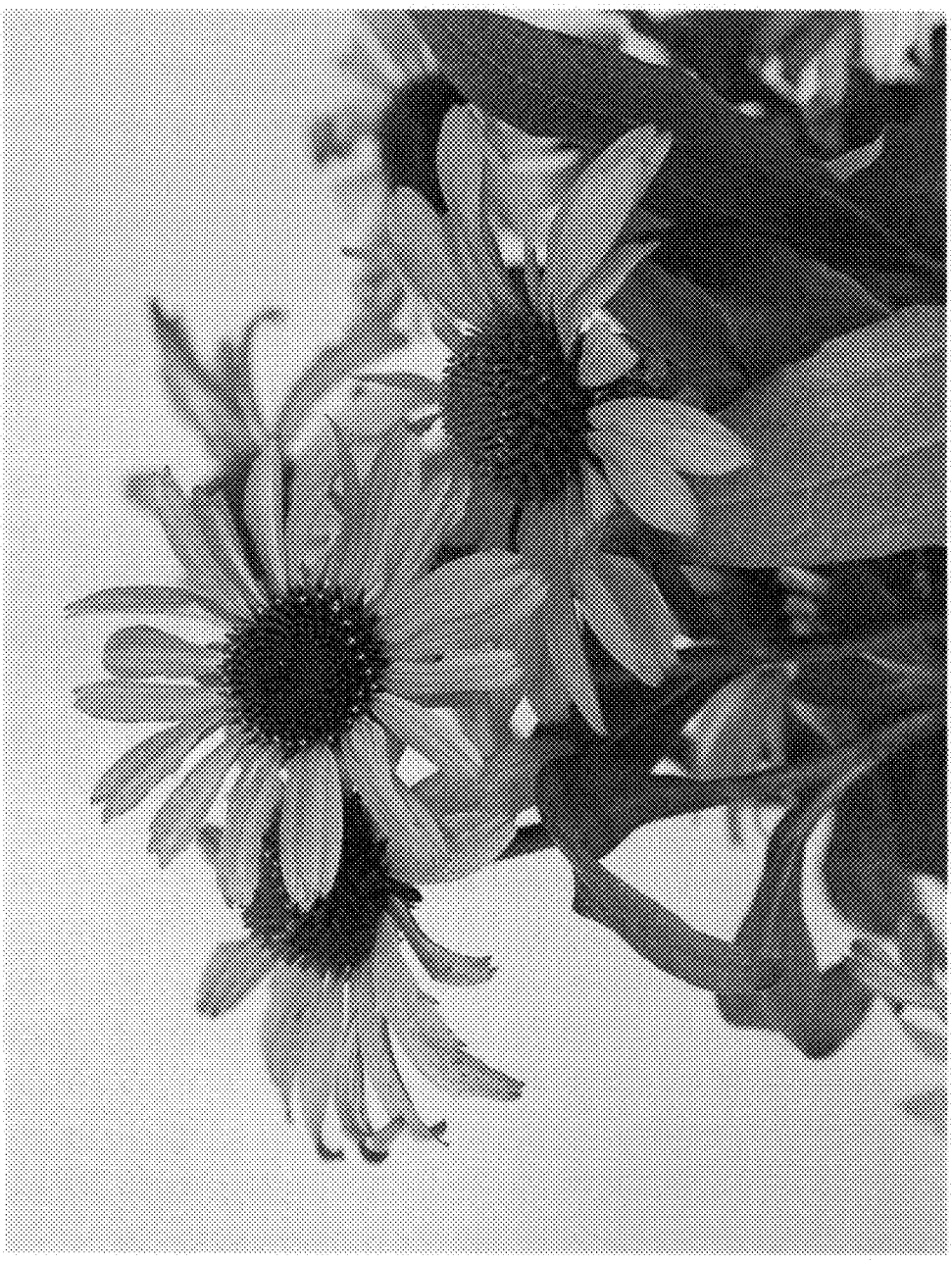

* * * * *